United States Patent
Yoshida et al.

(10) Patent No.: US 6,508,990 B1
(45) Date of Patent: Jan. 21, 2003

(54) SUBSTRATE TREATING METHOD AND APPARATUS

(75) Inventors: Haruo Yoshida, Tokyo (JP); Michiaki Endo, Tokyo (JP); Michio Niwano, 18-12, Sumiyoshidai Higashi 3-chome, Izumi-ku, Sendai-shi, Miyagi-ken, 981-3222 (JP); Nobuo Miyamoto, 26-15, Sakuragaoka 7-chome, Aoba-ku, Sendai-shi, Miyagi-ken, 981-0961 (JP); Yasuhiro Maeda, Tokyo (JP)

(73) Assignees: Advantest Corp., Tokyo (JP); Michio Niwano, Miyagi (JP); Nobuo Miyamoto, Miyagi (JP)

( * ) Notice: Subject to any disclaimer, the term of this patent is extended or adjusted under 35 U.S.C. 154(b) by 0 days.

(21) Appl. No.: 09/354,054

(22) Filed: Jul. 15, 1999

(30) Foreign Application Priority Data

| Jul. 16, 1998 | (JP) | ............................................ 10-202018 |
| Jul. 16, 1998 | (JP) | ............................................ 10-202090 |
| May 31, 1999 | (JP) | ............................................ 11-151919 |

(51) Int. Cl.[7] ........................ B01J 19/08; B01J 19/12; G05B 1/00; G01N 21/00; G01N 31/00
(52) U.S. Cl. ...................... 422/186.05; 422/292; 422/3; 422/62; 422/82.05; 422/82.09; 422/82.11; 134/1; 134/1.2; 134/1.3; 134/18; 356/239.7; 356/239.8; 356/432
(58) Field of Search ......................... 422/3, 62, 186.05, 422/292, 82.05, 82.09, 82.11; 134/1, 1.2, 1.3, 18; 356/239.7, 239.8, 432

(56) References Cited

U.S. PATENT DOCUMENTS

| 5,005,108 A | * | 4/1991 | Pritash et al. .................. 362/31 |
| 5,539,514 A | * | 7/1996 | Shishido et al. ............. 356/237 |
| 5,669,979 A | * | 9/1997 | Elliot et al. ..................... 134/1 |

* cited by examiner

Primary Examiner—Robert J. Warden, Sr.
Assistant Examiner—Imad Soubra
(74) Attorney, Agent, or Firm—Muramatsu & Associates

(57) ABSTRACT

A substrate treating method and apparatus which can perform in-situ monitoring of surface state of a semiconductor substrate. The substrate treating apparatus comprises substrate treating means for subjecting the substrate to a required treatment, means for condensing infrared radiation emitted by an infrared radiation source onto an outer peripheral part of the substrate and introducing the infrared radiation into the substrate, means for detecting the infrared radiation which has undergone multiple reflection inside the substrate and exited from the substrate, means for analyzing the detected infrared radiation, means for monitoring the surface state of the substrate, and control means for controlling the substrate treating means, based on the monitored surface state of the substrate.

19 Claims, 11 Drawing Sheets

SUBSTRATE OUTER PERIPHERAL PART

SUBSTRATE OUTER PERIPHERAL PART

INFRARED RADIATION

| POINT | x | y |
|---|---|---|
| A | 75 μm | 0 μm |
| B | 500 μm | 0 μm |
| C | 50 μm | 258 μm |
| D | 0 μm | 75 μm |

SUBSTRATE TREATING METHOD AND APPARATUS

BACKGROUND OF THE INVENTION

The present invention relates to a substrate treating method and apparatus for subjecting a semiconductor substrate to a required treatment, more specifically to a substrate treating method and apparatus which can perform in-situ monitoring of surface states of a semiconductor substrate at a fabrication site and, based on results of the in-situ monitoring, can control treating conditions or detect the end point of the treatment.

Recently, semiconductor devices have elements increasingly micronized, and are made increasingly three dimensional. This makes it difficult for cleaning solutions to intrude into micronized regions or steep steps or to be replaced there. In consideration of future further micronization, dry cleaning, which uses no chemical liquid is noted.

The dry cleaning is art that radiation, e.g., UV radiation for decomposing or dissociating contaminants is applied to a semiconductor substrate, or active species are introduced while the UV radiation is being applied to thereby decompose and remove the contaminants adhered to the semiconductor substrate. For example, to remove organic contaminants staying on silicon substrates reaction with ozone or oxygen excited by UV radiation is effective. Oxygen molecules are dissociated to oxygen atoms by light of a below 242 nm wavelength. The organic contaminants are oxidized by the oxygen atoms and decomposed into $H_2O$, $O_2$, CO, $Co_2$, etc. of high vapor pressures. Organic bonds, such as C—C, C—H, C—O, etc. can be dissociated by the UV radiation. Thus, the contaminants on the semiconductor substrate can be removed.

Thus, knowing surface states of semiconductor substrates is very important also to control parameters for the dry cleaning, such as an optimum irradiation intensity, wavelength, oxygen amount, etc. Accordingly, a dry cleaning method and apparatus which enable in-situ monitoring of surface states of a semiconductor substrate at the fabrication site and control of operation parameters based on results of the in-situ monitoring are required.

On the other hand, plasma etching technique is widely used in patterning steps for forming device structures on semiconductor substrates. Recently, semiconductor devices have elements increasingly micronized, and are made increasingly three dimensional. This makes it difficult for cleaning solutions to intrude into micronized regions or steep steps or to be replaced there. Under these circumstances, dry cleaning using plasma etching is noted as a cleaning method using no chemical solutions.

Here, the plasma etching is dry etching using reactive gas plasmas and removes substances-to-be-treated mainly by actions of neutral active species.

The plasma etching process is determined by dynamic balance in adsorption, reaction and elimination processes between influxes of radical ions, etc. fed in gas phase and outfluxes from semiconductor substrate surfaces. In the plasma etching process, to set optimum plasma etching conditions and to detect the end point of the plasma etching, it is very effective to know adsorption states, chemical bonding states, structures and thicknesses of reaction layers, etc. of surface states of semiconductor substrates. Accordingly, a plasma etching method and apparatus which enable in-situ monitoring of surface states of a semiconductor substrate at the fabrication site and control of operation parameters based on results of the in-situ monitoring are required.

Thus, knowing surface states of semiconductor substrates is required not only in the dry cleaning and the plasma etching but also in other various sites. Various monitoring methods have been conventionally proposed, and some have been practiced.

Means for monitoring a surface state of a semiconductor substrate by internal multiple reflection of infrared radiation is provided by, e.g., FT-IR (Fourier-transform spectroscopy) apparatus or the special use marketed by Perkin-Elmer Co., U.S.A. For wider applications of the means Graseby Specac Limited, for example, markets various accessories.

In the conventional surface state monitoring method using this means, as exemplified in FIG. 11A, a substrate-to-be-treated 102 is cut into, e.g., a 40 mm×10 mm strip, and infrared radiation emitted from an infrared radiation source 104 is passed through the substrate-to-be-treated 102 to monitor states of the substrate surfaces. Otherwise, as exemplified in FIG. 11B, a substrate-to-be-treated 102 has the end tapered, and infrared radiation is incident on the end surface of the substrate-to-be-treated 102 to undergo multiple reflection inside the substrate, whereby a surface state of the substrate is monitored. Otherwise, as exemplified in FIG. 1C, infrared radiation is incident on a substrate-to-be-treated via a prism 106 positioned above the substrate to undergo multiple reflection inside the substrate, whereby a surface state of the substrate is monitored.

However, these monitoring methods needs cutting a substrate-to-be-treated into strips, additionally processing the substrate-to-be-treated, or disposing a prism above a substrate-to-be-treated. These monitoring methods have not been usable in the in-situ monitoring at site of fabricating semiconductor devices.

Methods of monitoring organic contaminants on semiconductor substrates are known, such as thermal desorption GC/MS (Gas Chromatography/Mass Spectroscopy), APIMS (Atmospheric Pressure Ionization Mass Spectroscopy), TDS (Thermal Desorption Spectroscopy), etc. However, these methods are not suitable to be used in-situ monitoring at site of fabricating semiconductor devices for reasons that these methods cannot directly observe large wafers of, e.g., above 300 mm-diameters which are expected to be developed, and need vacuum ambient atmosphere, and have low throughputs, and other reasons.

As described above, the above-described conventional monitoring methods, which are destructive, are not usable in the in-situ monitoring at site of fabricating semiconductor devices or are not suitable for monitoring large semiconductor wafers. These method are unapplicable not only to the in-situ monitoring of surface states of a semiconductor substrate for controlling operation parameters for the dry cleaning, but also to the in-situ monitoring of surface states of a semiconductor substrate for controlling operation parameters for the plasma etching.

The apparatuses for the above-described conventional dry cleaning and plasma etching includes no suitable means for confirming whether or not each substrate has reached prescribed values in actual steps, so that the dry cleaning and plasma etching are completed after set periods of time or whether all substrates have reached prescribed values. Accordingly, the treatments are not sufficient, and residues are generated, or excessive treatments are performed, damaging the substrates. The excessive treatments are not preferable in view of throughputs.

SUMMARY OF THE INVENTION

An object of the present invention is to provide a substrate treating method and apparatus which enable the in-situ monitoring of surfaces states of a semiconductor substrate at the fabrication site and the control operation parameters based on results of the monitoring, and can detect the end point of the treatment.

The above-described object is achieved by a substrate treating apparatus comprising: a substrate treating means for subjecting a substrate-to-be-treated to a required treatment; a surface state monitoring means including an infrared radiation condensing means for condensing infrared radiation or near-infrared radiation emitted by an infrared radiation source onto an outer peripheral part of the substrate-to-be-treated, an infrared radiation detecting means for detecting the infrared radiation or near-infrared radiation which has undergone multiple reflection inside the substrate-to-be-treated and exited from the substrate-to-be-treated, and an infrared radiation analyzing means for analyzing the infrared radiation or near-infrared radiation detected by the infrared radiation detecting means, the surface state monitoring means monitoring in-situ a surface state of the substrate-to-be-monitored when the substrate-to-be-treated is treated by the substrate treating means; and a control means for controlling the substrate treating means, based on the surface state of the substrate-to-be-treated, which was monitored by the surface state monitoring means. A substrate-to-be-treated can have the surface monitored uncontiguously and non-destructively without being deformed or damaged, being subjected to extra chemical etching, processing of the end surface, etc. or introducing infrared radiation or near-infrared radiation through optical members, such as prisms positioned above the substrate-to-be-treated. Accordingly, surface states of a substrate-to-be-treated are in-situ monitored at site of the fabrication, and operation parameters are controlled based on results of the surface state monitoring, so that the substrate-to-be-treated can be treated always under optimum conditions.

In the above-described substrate treating apparatus, it is possible that the infrared radiation analyzing means monitors the surface state of the substrate-to-be-treated, based on a spectroscopic results given by Fourier transform spectroscopy.

In the above-described substrate treating apparatus, it is possible that the infrared radiation analyzing means monitors the surface state of the substrate-to-be-treated, based on a spectroscopic result given by infrared spectroscopy using a diffraction lattice.

In the above-described substrate treating apparatus, it is possible that the substrate treating means is a cleaning means for decomposing and removing a contaminant adhered to the substrate-to-be-treated by light irradiation, the surface state monitoring means monitors a kind and/or an amount of the contaminant adhered to the substrate-to-be-treated, and the control means controls treating conditions for treating the substrate-to-be-treated by the cleaning means, based on the kind and/or the amount of the contaminant given by the surface state monitoring means.

In the above-described substrate treating apparatus, it is possible that the control means controls an irradiation intensity or an irradiation period of time of the light to be irradiated to the substrate-to-be-treated, based on the kind and/or the amount of the contaminant given by the surface state monitoring means.

In the above-described substrate treating apparatus, it is possible that the cleaning means includes an active species supply means for supplying an active species which reacts with the contaminant.

In the above-described substrate treating apparatus, it is possible that the control means controls a supply amount of the active species to be supplied by the active species supply means, based on the kind and/or the amount of the contaminant given by the surface state monitoring means.

In the above-described substrate treating apparatus, it is possible that the apparatus further comprises an end point detecting means for detecting an end point of the substrate treatment, based on the kind and/or the amount of the contaminant given by the surface state monitoring means.

In the above-described substrate treating apparatus, it is possible that the end point detecting means judges whether or not the substrate-to-be-treated has arrived at the end point by comparing a monitored level of resonance absorption intensity of the infrared radiation or near-infrared radiation of the contaminant with a prescribed reference level.

In the above-described substrate treating apparatus, it is possible that the substrate treating means is an etching means for etching the substrate-to-be-treated by using a plasma; and the control means controls etching conditions for etching the substrate-to-be-treated by the etching means, based on the surface state of the substrate-to-be-treated monitored by the surface state monitoring means.

In the above-described substrate treating apparatus, it is possible that the control means controls a state of the plasma, based on the surface state of the substrate-to-be-treated monitored by the surface state monitoring means.

In the above-described substrate treating apparatus, it is possible that the surface state monitoring means monitors an adsorption state of an influx or an outflux, a chemical bonding state or a structure of a reactive layer on the surface of the substrate-to-be-treated.

In the above-described substrate treating apparatus, it is possible that the surface state monitoring means monitors a kind and/or an amount of a contaminant adhered to the surface of the substrate-to-be-treated.

In the above-described substrate treating apparatus, it is possible that the apparatus further comprises an end point detecting means for detecting an end point of the etching, based on the surface state of the substrate-to-be-treated monitored by the surface state monitoring means.

In the above-described substrate treating apparatus, it is possible that the control means stops the treatment of the substrate-to-be-treated, based on end point information given by the end point detecting means.

In the above-described substrate treating apparatus, it is possible that the substrate-to-be-treated has a declined part on the outer peripheral part, which is formed by chamfering the corner defined by the surface of the substrate-to-be-treated and an outer peripheral surface thereof; the infrared radiation condensing means condenses the infrared radiation or near-infrared radiation onto the declined part of the substrate-to-be-treated.

In the above-described substrate treating apparatus, it is possible that the infrared radiation condensing means condenses the infrared radiation or near-infrared radiation into a circular or an empirical focus.

In the above-described substrate treating apparatus, it is possible that the infrared radiation source is an explosion-proof type infrared radiation source having a light source for emitting the infrared radiation or near-infrared radiation sealed in a vessel.

The above-described object is also achieved by a substrate treating method for subjecting a substrate-to-be-treated to a required treatment comprising: condensing infrared radiation or near-infrared radiation onto an outer peripheral part of a substrate-to-be-treated before treating the substrate-to-be-treated or in treating the substrate-to-be-treated and introducing the infrared radiation or near-infrared radiation; detecting the infrared radiation or near-infrared radiation which has undergone multiple reflection in the substrate-to-be-treated and exited from the substrate-to-be-treated; analyzing the detected infrared radiation or near-infrared radiation to monitor a surface state of the substrate-to-be-treated; and controlling treating conditions for treating the substrate-to-be-treated by the required treatment in accordance with the monitored surface state of the substrate-to-be-treated.

The above-described object is also achieved by a substrate treating method for subjecting a substrate-to-be-treated to a required treatment comprising: condensing infrared radiation or near-infrared radiation onto an outer peripheral part of a substrate-to-be-treated in treating the substrate-to-be-treated and introducing the infrared radiation or near-infrared radiation; detecting the infrared radiation or near-infrared radiation which has undergone multiple reflection in the substrate-to-be-treated and exited from the substrate-to-be-treated; analyzing the detected infrared radiation or near-infrared radiation to monitor a surface state of the substrate-to-be-treated; and detecting an end point of the required treatment of the substrate-to-be-treated, based on the monitored surface state of the substrate-to-be-treated.

An end point of a treatment of a substrate-to-be-treated can be detected based on results of the surface state monitoring. A device being fabricated on the substrate-to-be-treated can be protected from damage. The substrate can be advanced to next processing without being excessively treated, and higher throughputs can be obtained. The treatment can have uniform quality.

In the above-described substrate treating method, it is possible that a monitored level of resonance absorption intensity of the infrared radiation or near-infrared radiation is compared with a prescribed reference level to judge whether or not the required treatment has reached the end point.

In the above-described substrate treating method, it is possible that the required treatment is for decomposing and removing a contaminant adhered to the substrate-to-be-treated by light irradiation; and in monitoring the surface state of the substrate-to-be-treated the contaminant adhered to the surface of the substrate-to-be-treated is monitored, and treatment conditions for the cleaning treatment are controlled in accordance with a monitored kind and/or amount of the contaminant.

In the above-described substrate treating method, it is possible that in the step of cleaning the substrate-to-be-treated, an active species reactive with the contaminant is supplied.

In the above-described substrate treating method, it is possible that a supply amount of the active species is controlled based on the surface state of the substrate-to-be-treated.

In the above-described substrate treating method, it is possible that an irradiation intensity or an irradiation period of time of the light to be irradiated to the substrate-to-be-treated is controlled based on the surface state of the substrate-to-be-treated.

In the above-described substrate treating method, it is possible that the required treatment is for etching the substrate-to-be-treated using a plasma, and conditions for the etching are controlled based on the monitored surface state of the substrate-to-be-treated.

In the above-described substrate treating method, it is possible that a state of the plasma is controlled based on the monitored surface state of the substrate-to-be-treated.

In the above-described substrate treating method, it is possible that the etching conditions are determined based on results of monitoring an adsorption state of an influx or an outflux, chemical bonding states or structures of reactive layers on the surface of the substrate-to-be-treated.

In the above-described substrate treating method, it is possible that the etching conditions are determined based on monitored results of a kind and/or an amount of the contaminant adhered to the surface of the substrate-to-be-treated.

In the above-described substrate treating method, it is possible that the infrared radiation or near-infrared radiation is incident on a declined part on the outer peripheral part of the substrate-to-be-treated, which is formed by chamfering the corner defined by the surface of the substrate-to-be-treated and an outer peripheral surface thereof and is introduced from the declined part into the substrate-to-be-treated.

In the above-described substrate treating method, it is possible that the infrared radiation or near-infrared radiation exited from the substrate-to-be-treated is spectroscoped by Fourier transform spectroscopy, and the contaminant is monitored based on a result of the spectroscopy.

In the above-described substrate treating method, it is possible that the infrared radiation or near-infrared radiation exited from the substrate-to-be-treated is spectroscoped by a diffraction lattice, and the contaminant is monitored based on a result of the spectroscopy.

In the above-described substrate treating method, it is possible that the monitoring is repeated plural times while the substrate-to-be-treated is being rotated to monitor the surface state of the substrate-to-be-treated substantially all over the surface of the substrate-to-be-treated, and the treating conditions of the substrate-to-be-treated are controlled based on the monitored surface state of the substrate-to-be-treated.

BRIEF DESCRIPTION OF THE INVENTION

DETAILED DESCRIPTION OF THE INVENTION

[First Embodiment]

The substrate treating method and apparatus according to a first embodiment of the present invention will be explained with reference to FIGS. 1 to 9.

Figure 1:
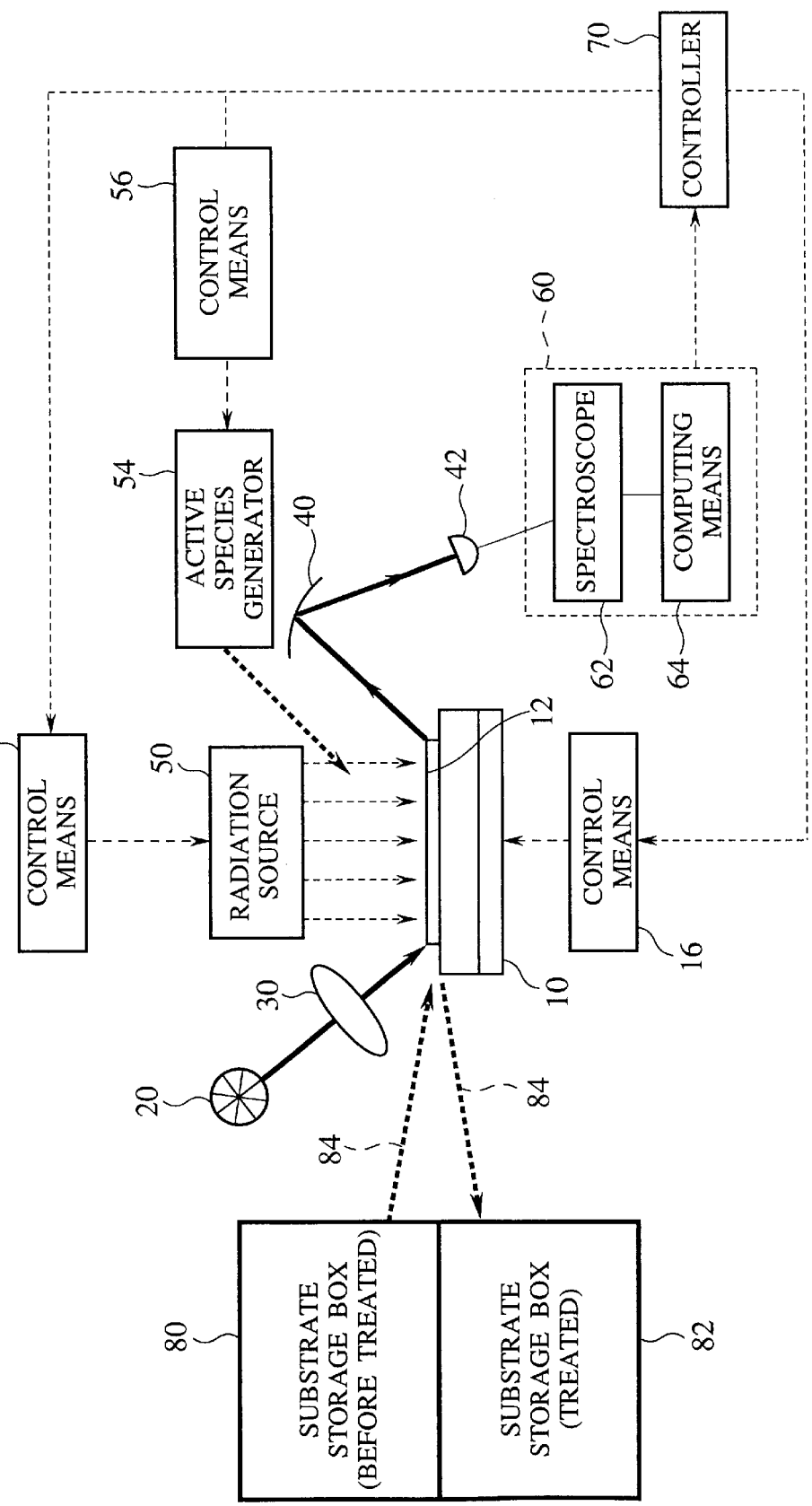
FIG. 1 is a diagrammatic view of the substrate treating apparatus according to a first embodiment of the present invention, which shows a structure thereof.
Figure 2:
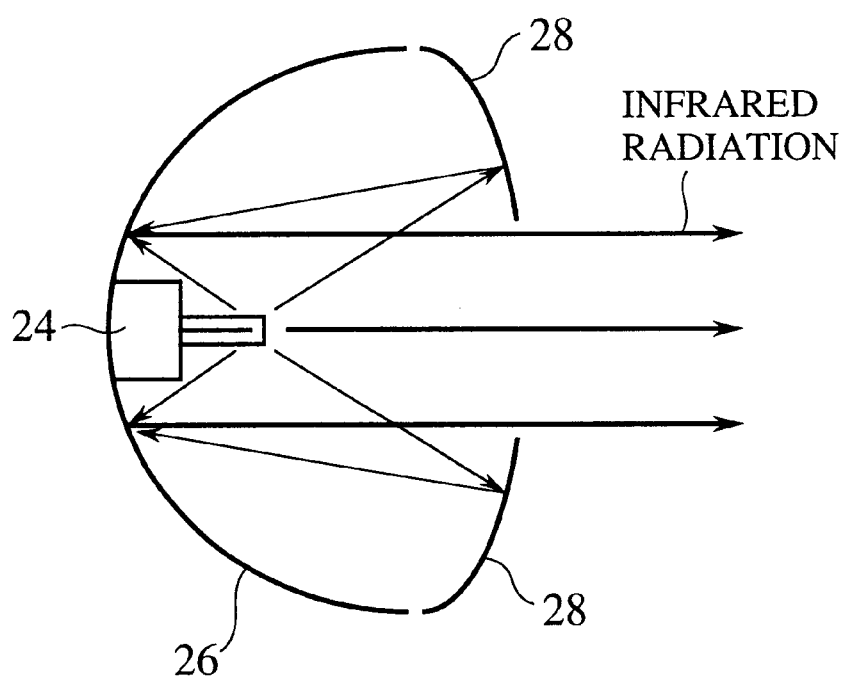
FIG. 2 is a schematic sectional view of the infrared radiation source of the substrate treating apparatus according to the first embodiment of the present invention.
Figure 3A:
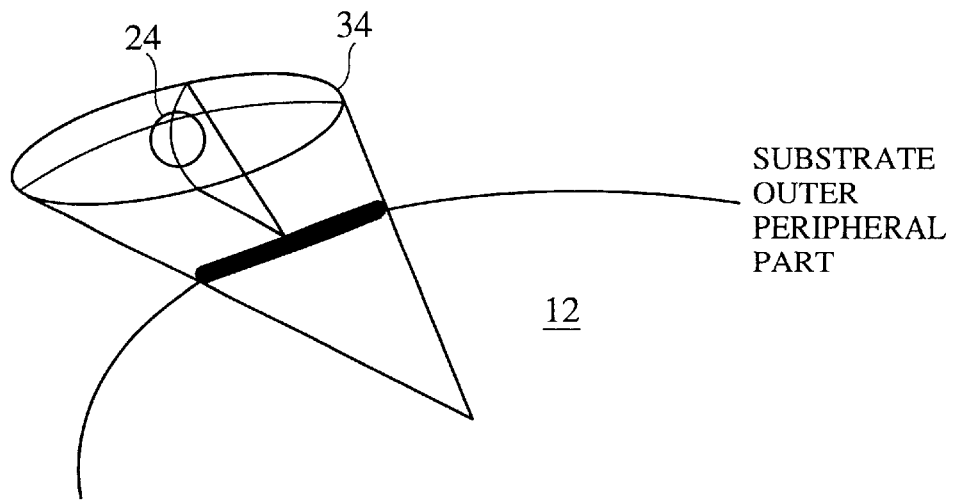
FIGS. 3A and 3B are views explaining a method for condensing infrared radiation on the outer periphery of the substrate-to-be-treated by means of a concave mirror.
Figure 3B:
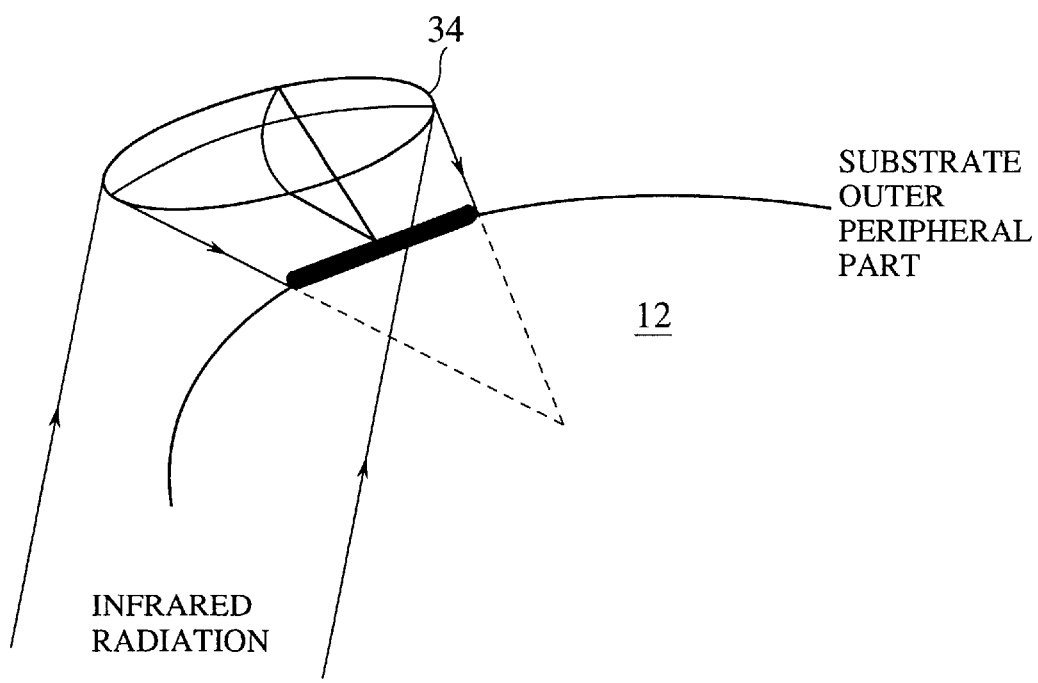
Figure 4A:
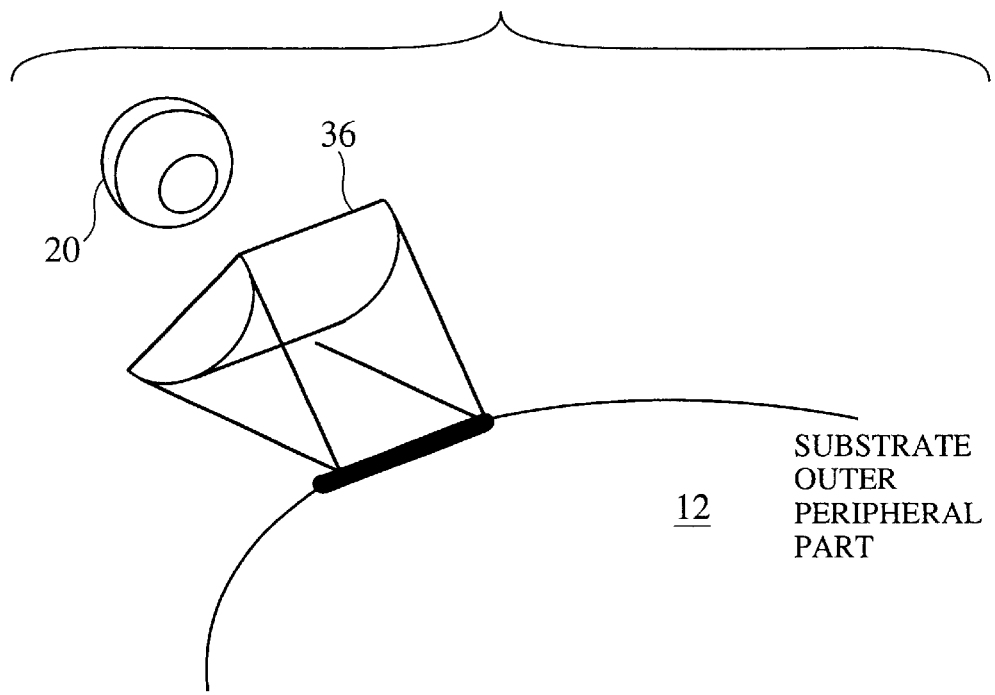
FIGS. 4A and 4B are views explaining a method for condensing infrared radiation on the outer periphery of the substrate-to-be-treated by means of a cylindrical lens or a slit
Figure 4B:
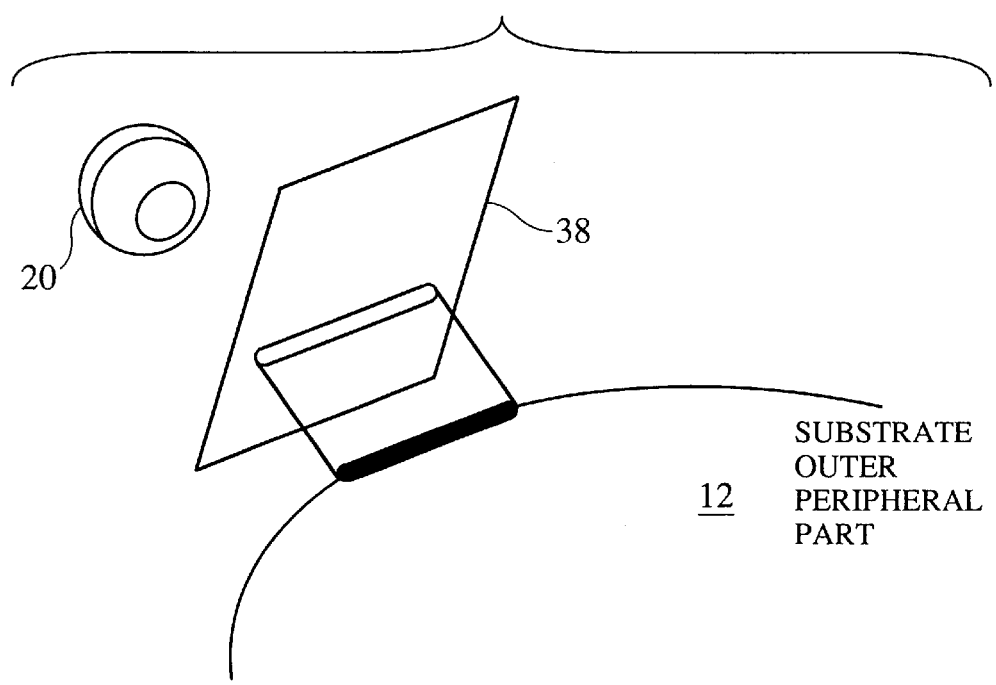
Figure 5:
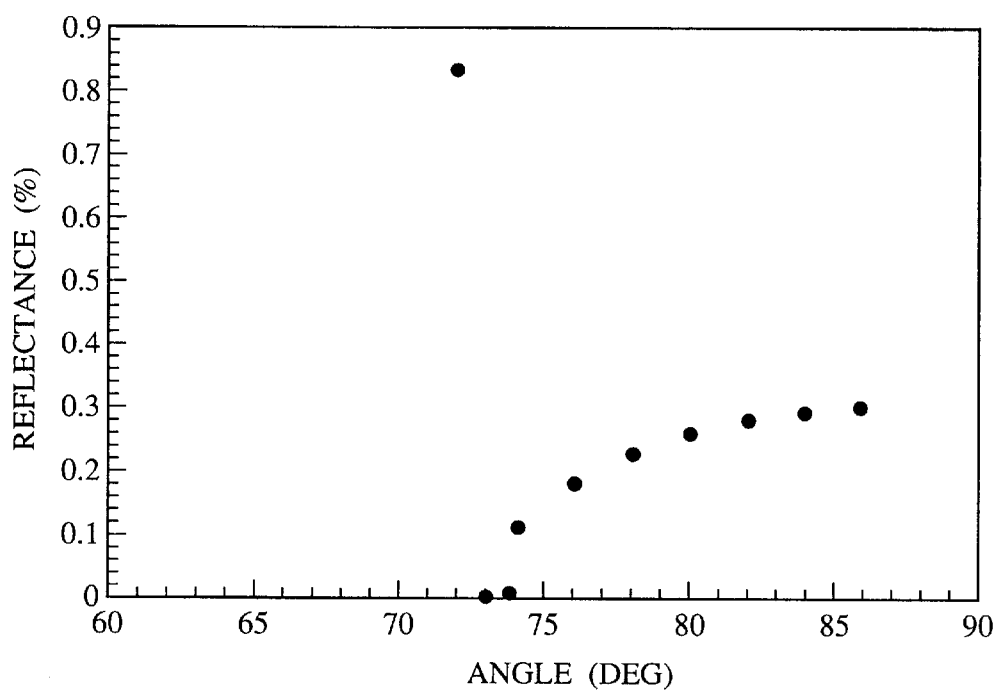
FIG. 5 is a graph of incident angle dependency of energy reflectances when infrared radiation exits from the interior of a silicon substrate into air.
Figure 6:
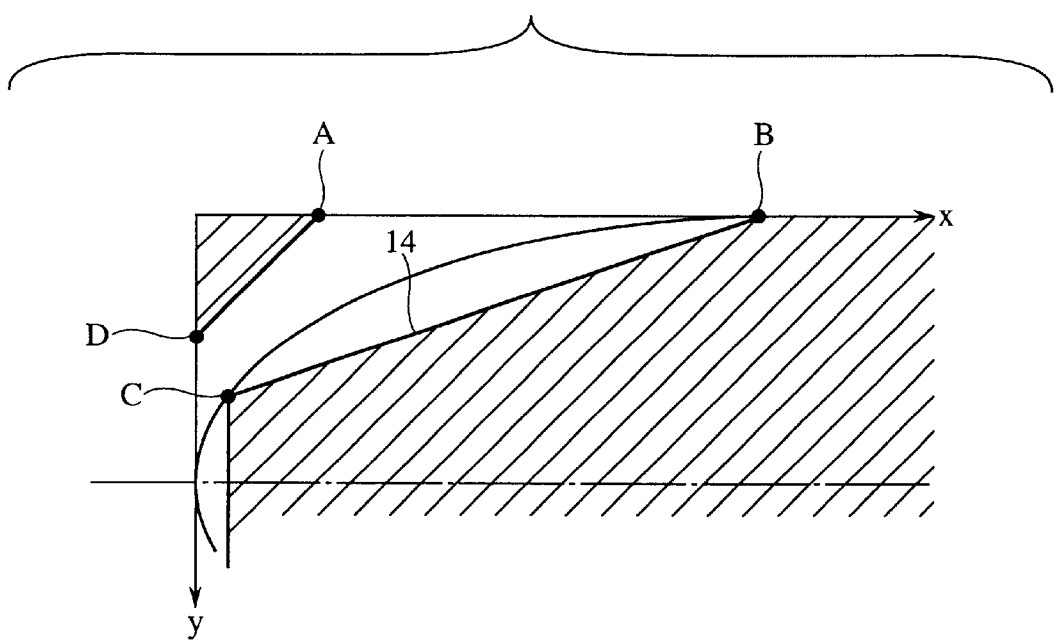
FIG. 6 is a view showing a configuration of the circumferential edge of a 300 mm-wafer in accordance with SEMI Standard Specifications.
Figure 7:
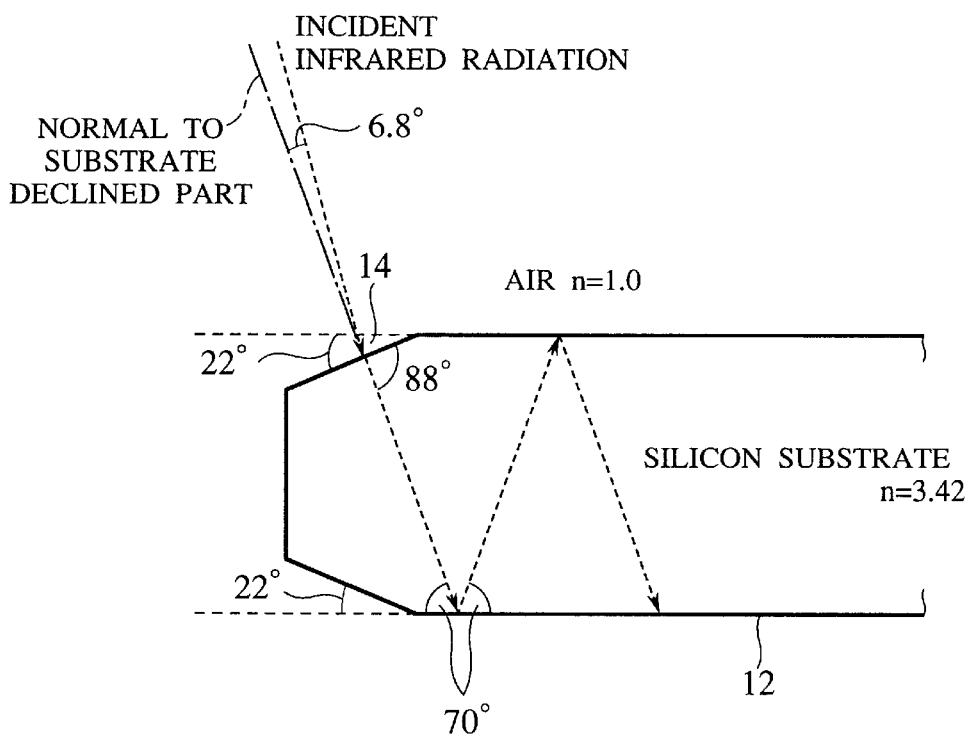
FIG. 7 is a view explaining setting an incident angle of infrared radiation on the substrate-to-be-treated in the substrate treating method and apparatus according to the first embodiment of the present invention.
Figure 8:
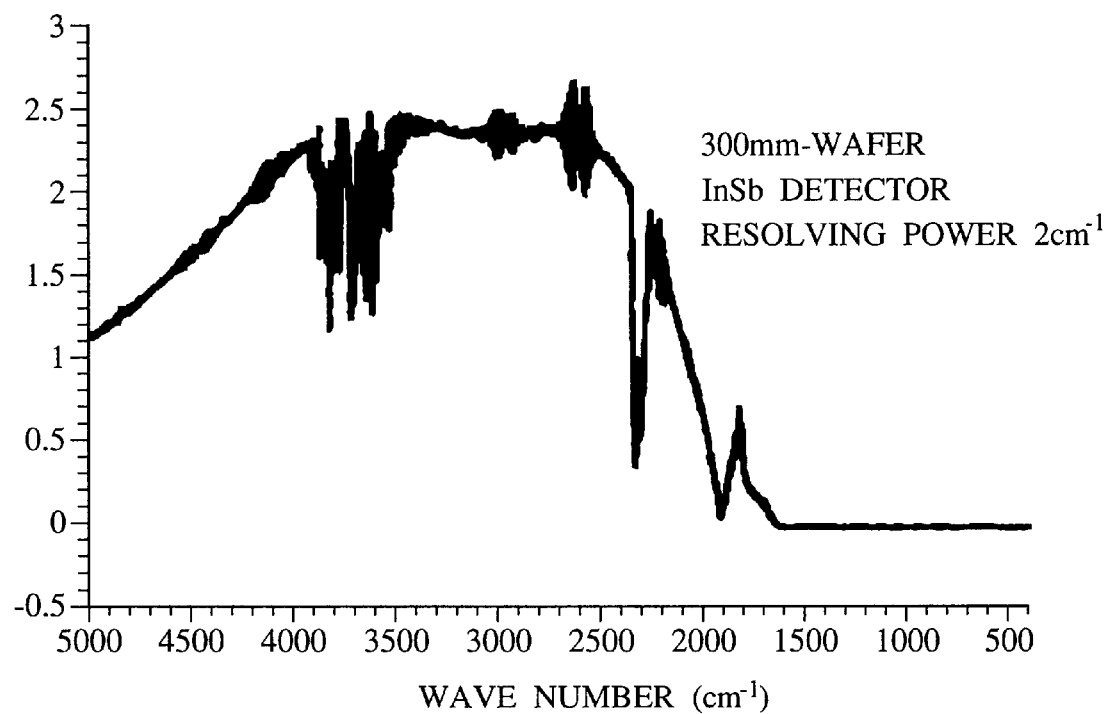
FIG. 8 is a graph of internal multiple reflection spectra of a 300 mm-wafer.
Figure 9:
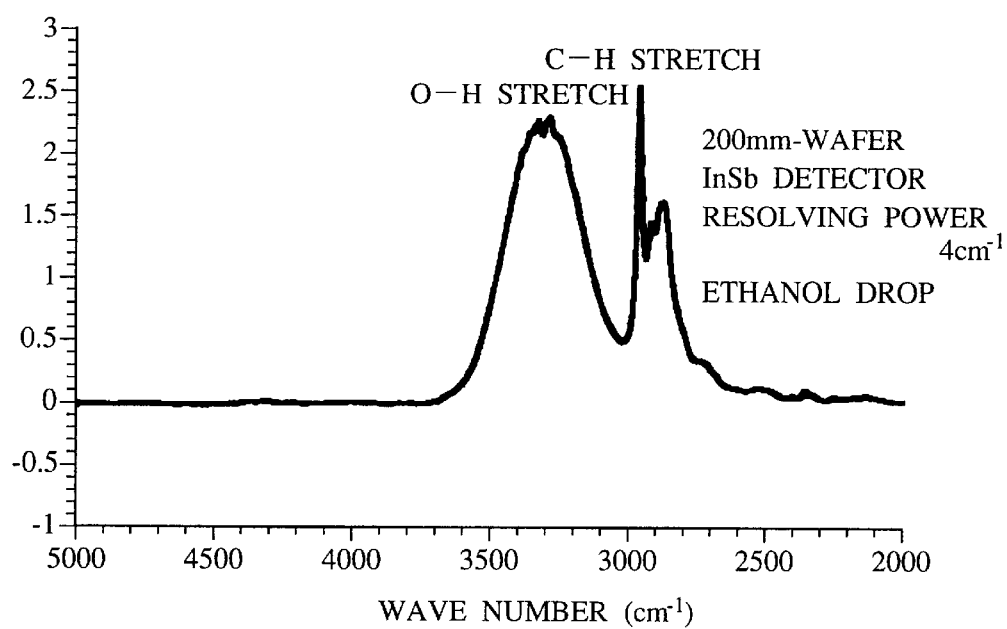
FIG. 9 is a graph of adsorption spectra obtained by the internal multiple reflection of the substrate-to-be-treated.

FIG. 1 is a diagrammatic view of the substrate treating apparatus according to the present embodiment. FIG. 2 is a diagrammatic sectional view of an infrared radiation source of the substrate treating apparatus according to the present embodiment. FIGS. 3A–3B are views explaining a method for condensing infrared radiation by a concave mirror along the outer periphery of a substrate-to-be-treated. FIGS. 4A–4B are views explaining a method for condensing infrared radiation by a cylindrical lens or a slit along the outer periphery of a substrate-to-be-treated. FIG. 5 is a graph of incident angle dependency of energy reflectivities at the time that the infrared radiation is emitted from the interior of a silicon substrate into air. FIG. 6 is a view of a configuration of the peripheral edge of a 300 mm-wafer in accordance with SEMI standard specifications. FIG. 7 is a view explaining a method for setting an incident angle of infrared radiation on a substrate-to-be-treated, which is used in the substrate treating method and apparatus according to the present embodiment. FIG. 8 is a graph of spectra of internal multiple reflection inside the 300 mm-wafer. FIG. 9 is a graph of absorption spectra given by the internal multiple reflection inside the substrate-to-be-treated.

[1] General Structure of the Apparatus

The substrate treating apparatus according to the present embodiment will be diagrammatically explained with reference to FIG. 1. In the present embodiment the present invention is applied to a dry cleaning apparatus.

A substrate-to-be-treated 12 which is to be subjected to the dry cleaning is mounted on a substrate mount 10. A radiation source 50 for irradiating energy radiation, such as UV radiation, to dissociate bonds of organic substances is disposed above the substrate mount 10. An active species generator 54 for generating active species (e.g., ozone or oxygen in the atomic state), which reacts with organic substances on the substrate-to-be-treated 12 and decomposes them is disposed near the substrate-to-be-treated 12.

Near the substrate-to-be-treated 12, there is provided an infrared radiation optical system including an infrared radiation source 20 which emits infrared radiation or near-infrared radiation, infrared radiation condensing means 30 which condenses (focuses) infrared radiation or near-infrared radiation emitted by the infrared radiation source 20 to apply the infrared radiation or the near-infrared radiation to the substrate-to-be-treated 12, infrared radiation condensing means 40 which condenses (focuses) the infrared radiation or near-infrared radiation which has undergone multiple reflection inside the substrate-to-be treated 12 and exited from the substrate-to-be-treated 12, and an infrared radiation detector 42 which detects the infrared radiation or the near-infrared radiation condensed by the infrared radiation condensing means 40.

The infrared radiation detector 42 is connected to an infrared radiation analyzing means 60 which analyzes surface states of the substrate-to-be-treated 12, based on detected signals produced by the infrared radiation detector 42. The infrared radiation analyzing means 60 includes a spectroscope 62 which spectroscopes infrared radiation or near-infrared radiation detected by the infrared radiation detector 42, and computing means 64 which stores data to be used in analyzing surface states and judging an end point of the operation and conducts prescribed computations, based on the data and result outputs from the spectroscope 62. The infrared radiation analyzing means 60 is connected to the radiation source 50 through a controller 70 and a radiation source control means 52, connected to an active species generator 54 through the controller 70 and an active species generator control means 56 and connected to the substrate mount 10 through the controller 70 and a substrate mount control means 16, so that the radiation source 50, the active species generator 54 and the substrate mount 10 can be controlled, based on a result of the analysis of the infrared radiation analyzing means 60.

In the optical path of the infrared radiation detector 42 and the optical path of infrared radiation to be detected, there are provided means (not shown) for removing carbon dioxide ($CO_2$) in air, whose spectra overlap those of organic molecules. Near the substrate mount 10, there are provided substrate storage boxes 80, 82 which store substrates-to-be-treated 12 after and before the treatment, and a substrate convey system 84 which conveys substrates-to-be-treated stored in the substrate storage box 80 to mount the same on the substrate mount 10, or conveys the dry-cleaned substrates-to-be-treated from the substrate mount 10 to the substrate storage box 82.

As described above, the substrate treating apparatus according to the present embodiment is characterized by the infrared radiation optical system in which infrared radiation is caused to undergo multiple reflection inside a substrate-to-be-treated 12 to thereby monitor surface states of the substrate-to-be-treated 12. Especially, the infrared radiation optical system according to the present embodiment is applied, whereby organic contamination and chemical contamination on a substrate-to-be-treated 12 can be in-situ monitored without performing additional processing, such as chemical etching, on the substrate or without passing infrared radiation into the substrate through the prism disposed above the substrate-to-be-treated 12.

The substrate treating apparatus including such infrared radiation optical system enables the in-situ monitoring of surface states of a substrate-to-be-treated 12 in the dry cleaning step, whereby operation parameters can be suitably controlled based on results of the monitoring so that the dry cleaning can be always performed in optimum conditions. Based on the monitoring results an end point of the dry cleaning can be detected.

Then, the respective constituent members of the substrate treating apparatus according to the present embodiment will be detailed with reference to FIGS. 1 to 7. The details of the monitoring system are given to the specification of Japan Patent Application No. 95853/1999. The various monitoring systems described in the specification are applicable to the substrate treating method and apparatus according to the present embodiment.

(a) Radiation Source 50, Active Species Generator 54

The radiation source 50 is for dissociating and evaporating organic contaminants adhered to the surface of a substrate-to-be-treated 12 and emits radiation of higher energy than bonding energy of the adhered organic contaminants. The radiation source 50 may be a UV radiation source, such as Xe (xenon) excimer light, a low pressure mercury lamp having a 185 nm-emission wavelength and a 254 nm-emission wavelength, and an ultraviolet light source such as a dielectric barrier discharge excimer lamp having a 172 nm-emission wavelength or others. The radiation of such energy is applied to the surface of the substrate-to-be-monitored 12, whereby the bonds of organic contaminants, such as C—C, C—H, C—O, etc. can be dissociated to be removed or evaporated from the surface of the substrate-to-be-treated 12.

Radiation to be emitted by the radiation source 50 can be suitably controlled by the controller 70 and the radiation source control means 52 in accordance with a result of the in-situ monitoring of surfaces states of the substrate-to-be-treated 12. For example, the radiation source 50 of, e.g., the type that the radiation can be irradiated in pulses may have a pulse duration and a pulse number controlled based on a result of the in-situ monitoring by the infrared radiation optical system, whereby only organic contaminants can be removed or evaporated without damaging a semiconductor device fabricated on the substrate-to-be-treated 12.

The radiation for removing the organic contaminants may be applied at once to the entire surface of the substrate-to-be-treated 12, or may be applied in a certain spot size to scan the entire surface of the substrate-to-be-treated 12 or the surface by a prescribed area to remove only organic contaminants in the area.

The active species generator 54, which supplies, such as ozone, oxygen in the atomic state, is for accelerating removal of contaminants from a substrate-to-be-treated 12 by the radiation source 50. Oxygen molecules are decomposed into oxygen atoms by radiation of a below 242 nm-wavelength. Oxygen atoms in the atomic state is applied to the surface of a substrate-to-be-treated 12 to oxidize organic contaminants adhered to the surface and decompose them into $H_2O$, $O_2$, CO, $CO_2$, etc. of high vapor pressure. Thus, cleaning is accelerated.

A supply amount (concentration) of active species to be supplied by the active species generator 54 can be controlled by the controller 70 and the active species generator control means 56, based on a result of the monitoring of surfaces states of a substrate-to-be-treated 12.

The radiation source 50 and the active species generator 54 may be the same as used in the usual dry cleaning apparatuses.

The dry cleaning of such mechanism is applicable not only to removal of organic contaminants but also to chemical contaminants, such as ammonium ($NH_3$), etc., which are generated from human bodies and AP (ammonium peroxide) cleaning solution.

(b) Infrared Radiation Source 20

As exemplified in FIG. 2, the infrared radiation source 20 comprises a light source 24 for generating infrared radiation, a rear reflecting plate 26 and a front, reflecting plate 28.

The light source 24 is provided by infrared radiation or near-infrared radiation of a 2–25 μm band corresponding to molecular vibrations of organic molecules. For example, heat rays emitted by applying current to silicon carbide (SiC) as a filament may be used as the light source 24. The light source of SiC, such as an SiC Globar lamp or others, has characteristics of emitting infrared radiation of a 1.1–25 μm band and; being usable naked in air without burning. Alkyl group, olefin, aromatic group, aldehyde., amide, amine, nitryl, sulfur oxides, carbon-oxygen bond, and nitrogen-oxygen bond, etc., have molecular vibration frequency corresponding to such infrared radiation range.

Infrared radiation or near-infrared radiation is used as a light source for the monitoring because infrared radiation intrinsically has the energy level lower in comparison with x-rays, γ-rays, accelerated electron beams, accelerated ion beams, etc., so that when infrared radiation is applied to an object-to-be-monitored, the possibility of the infrared radiation damaging the object-to-be-treated is very low. This is one reason why infrared radiation is selected as a probe beam source which does not damage delicate objects-to-be-treated, such as very highly integrated semiconductor devices in their fabrication processes. Another merit of the use of infrared radiation or near radiation is that a vibration frequency band of molecular vibrations of organic contaminants or chemical contaminants to be detected is substantially in the vibration frequency band of infrared radiation or near-infrared radiation.

The rear reflection plate 26 and the front reflection plate 28 function, as the members of the infrared radiation source, to improve efficiency of an effective infrared radiation amount with a constant current applied to. The rear reflection plate 26 and the front reflection plate 28 have the surfaces coated with a material which effectively reflects infrared radiation, e.g., aluminum or others.

The rear reflection plate 26 is constituted by a parabolic reflection plate and is disposed so that the light source 24 is positioned at a focus of the paraboloid. Thus, infrared radiation emitted by the light source 24 is transformed into substantially parallel rays.

The front reflection plate 28 is for prohibiting the generation of stray light unnecessary for the monitoring. The front reflection plate 28 as well as the rear reflection plate 28 are respectively constituted by a parabolic reflection plate. The front reflection plate 28 has an exit window through which exits only infrared radiation necessary for the monitoring. The front reflection plate 28 reflects infrared radiation unnecessary for the monitoring, whereby generation of stray light can be prevented. Infrared radiation reflected on the front reflection plate 28 is again reflected on the rear reflection plate 26, and some of the reflected infrared radiation is transformed into effective parallel rays, with a result of increase of effective infrared radiation. However, the front reflection plate 28 is not essential.

The exit window for the infrared radiation may be covered with an infrared radiation transmitting substance to seal in the light source, and the infrared radiation source may be made explosion-proof type. The explosion-proof type radiation source, in which the light source is covered by a vessel to be sealed from the active species, is necessary for the dry cleaning apparatus using the active species, e.g., ozone or oxygen, thereby preventing accident or explosion involved by the active species.

The following description will be made mainly by means of a case that the light emitted by the light source 24 is infrared radiation, but the present invention is also applicable to a case that the light emitted by the light source 24 is near-infrared radiation.

(c) Infrared Radiation Condensing Means 30

The infrared radiation condensing means 30 is to converge the infrared radiation before entering the substrate-to-be-monitored 12 as shown in FIGS. 3A and 3B. In the substrate treating apparatus according to the present embodiment, in monitoring surface states of a substrate-to-be-treated 12, infrared radiation is caused to enter a substrate-to-be-treated 12 through a part of the outer periphery of the substrate-to-be-treated 12. For this end, it is important for higher incidence efficiency of infrared radiation entering the substrate-to-be-treated to converge (condense) the infrared radiation emitted by the infrared radiation source 20 into a prescribed shape to apply the infrared radiation to the substrate-to-be-treated. It is preferable that infrared radiation is converged to an elliptical shape along the outer periphery of the substrate-to-be-treated.

To converge infrared radiation into an elliptical focal shape, an aberration of a lens system is intentionally used. An elongate focal shape can be formed by utilizing a coma aberration or distortion of a lens system. Here, a concave mirror 34 having a larger focal distance in the X direction than that in the Y direction is assumed. An elliptical focal shape can be formed on the outer periphery of the substrate-to-be-treated 12 by disposing the infrared radiation source 20 at the center of the concave mirror 34 (see FIG. 3A). When parallel rays are incident on the concave mirror 34 shown in FIG. 3A, reflected infrared radiation forms a focus in the longer axis (X direction) below the substrate-to-be-treated, and a focus in the shorter axis (Y direction) can be formed on the outer periphery of the substrate-to-be-treated (see FIG. 3B).

A focal shape of infrared radiation is preferably elliptical but may be circular. The circular focal shape is a little inferior to an elliptical focal shape in incidence efficiency. To form a circular focal shape a convex lens, for example, may be used.

It is possible that infrared radiation is transformed to an elongate focal shape to be applied to a substrate-to-be-treated 12. As exemplified in FIG. 4A, infrared radiation emitted by the infrared radiation source 20 may be converged by a cylindrical lens 36 or, as shown in FIG. 4B, may be passed through a slit 38 to be applied to.

(d) Arrangement of the Optical System

In the substrate treating apparatus according to the present embodiment, it is important to converge infrared radiation at one point on the outer periphery of a substrate-to-be-treated 12, cause the infrared radiation which has entered the substrate-to-be-treated to undergo internal multiple reflection, and again converge the infrared radiation which has exited from a point symmetrical to the incident point, so as to be guided to the infrared radiation detector 42. To this end, it is important how to cause the infrared radiation to efficiently enter the substrate-to-be-treated.

Then, conditions for the multiple reflection of infrared radiation inside a substrate-to-be-treated and conditions for causing infrared radiation to enter the substrate-to-be-treated from the outside will be explained.

In the substrate treating apparatus according to the present embodiment infrared radiation is caused to undergo multiple reflection inside a substrate-to-be-treated, detect molecular vibrations of organic contaminants or chemical contaminants, based on light exuded on the surfaces of the substrate-to-be-treated to monitor surface states of the substrate-to-be-treated. Accordingly, it is necessary that an incident angle of infrared radiation which enters a substrate-to-be-treated is set that the infrared radiation undergoes multiple reflection inside the substrate-to-be-treated 12.

Conditions for infrared radiation undergoes perfect reflection in a substrate-to-be-treated are given by computing Snell's law and energy reflectivities. In a case that the substrate-to-be-treated 12 is a silicon substrate, infrared radiation undergoes perfect reflection when infrared radiation forms angles of 0 to 72° (see FIG. 5). A trace of infrared radiation having an angle in this range is traced back, and an intersection between the end surface of the silicon substrate-to-be-treated and the infrared radiation is an incidence point of the infrared radiation on the silicon substrate.

The substrate treating apparatus according to the present embodiment can in-situ monitor a substrate-to-be-treated 12 without processing the substrate 12, and uses a processed configuration of an end surface of the commercially available substrate for the incidence of infrared radiation.

The configurations of the end surfaces of the semiconductor substrates are determined by SEMI (Semiconductor Equipment and Material International), and specifications of 300 mm-silicon wafers which are to be used around 2001 have been provisionally decided. The incident angle of the infrared radiation will be explained by means of a case that a 300 mm-silicon wafer is used.

The end surface configuration of a 300 mm-silicon wafer decided by the SEMI standard specifications is as shown in FIG. 6. That is, a 300 mm-silicon wafer is formed in a disc having a 300 mm-diameter and a 775 $\mu$m-thick and has the borders between a pair of surfaces and the outer peripheral surface chamfered. As shown in FIG. 7, the finished processed configuration of the wafer has an angle of about 22° formed by the line A-B and the line C-B. The region which is not hatched is an allowable range for configuration processing.

When it is assumed that an incident angle of infrared radiation propagating in the substrate is 70°, and a trace of the infrared radiation is traced back to set an incident point of the infrared radiation at an intersection of the infrared radiation and an end surface (the inclined portion 14 between B and C herein after called "a declined part" or "an end part") of the silicon substrate, as shown in FIG. 7, an angle formed by the declined part 14 and the infrared radiation is about 88°. Accordingly, when the angle is calculated back based on Snell's law where a refractive index of the silicon substrate is 3.42; a refractive index of air is 1.00; and an angle formed by a normal of the declined part 14 and infrared radiation is 2°, it is found that infrared radiation is incident at an angle of about 6.8° (about 74.8° to the flat surfaces of the substrate) to the normal of the declined part 14 so that the infrared radiation entering the silicon substrate undergo multiple reflection. At this time, an energy reflectivity at the incident point is as high as about 29.42%, but infrared radiation is irradiated in an irradiation intensity which compensates the high reflectivity.

An incident angle of infrared radiation incident on the declined part 14 can be decided by thus calculating back the incident angle, based on angles of multiple reflection in the substrate.

Even in the cases of semiconductor substrates other than the silicon substrate and of end surface configurations different from that described above, incident angles of infrared radiation can be set by the same procedure noted above. Infrared radiation may be incident on the declined part 14 of the front surface of the substrate or the declined part 14 of the back surface of the substrate. The infrared radiation may be incident simultaneously on the front and the back surfaces.

Another method of causing infrared radiation to enter a substrate is detailed in the specification of Japanese Patent Application No. 95853/1999 owned by the assignee of the present application.

(e) Substrate Mount 10

When a substrate-to-be-treated 12 is placed on the substrate mount 10 by a substrate carrier system, it is not always that the substrate-to-be-treated 12 is correctly positioned.

Then, a substrate mount control means 16 for finely adjusting the substrate mount 10 in X-, Y- and Z-directions is connected to the substrate mount 10. Fine adjustments in the X-, Y- and Z-directions are for aligning the optical axis of the infrared radiation so that, when the infrared radiation undergoes multiple reflection inside the substrate-to-be-treated 12 a maximum light amount can be fed to the infrared radiation detector 42.

An optimum point of a fine adjustment of the substrate mount 10 with a substrate-to-be-treated 12 mounted on, in the X-, Y- and Z-directions is judged based on a point where a maximum light amount of the infrared radiation which has undergone multiple reflection in the substrate-to-be-treated is detected, and can be automatically positioned. The positioning is performed by the controller 70 connected to the substrate mount 10.

Furthermore, the substrate mount 10 includes a rotary mechanism (not shown). A substrate-to-be-treated 12 is rotated so that substantially entire surface of a substrate-to-be-treated 12 can be detected for organic contaminants and chemical contaminants.

(f) Infrared Radiation Condensing Means 40

The infrared radiation incident on a substrate-to-be-treated is exited from a position symmetrical to the incident point. Then, the infrared radiation condensing means 40 condenses (converges or focuses) the infrared radiation exited from the substrate-to-be-treated 12 and guides the infrared radiation to the infrared radiation detector 42.

The infrared radiation condensing means 40 comprises, e.g., a concave mirror and a reflecting mirror. The infrared radiation condensing means 40 of this structure can condense the infrared radiation exited from the substrate-to-be-treated 12 by the concave mirror and guide the same to the infrared radiation detector 42 via the reflecting mirror. A convex lens may be used in place of the concave mirror, and infrared radiation is condensed by passing through the convex lens.

(g) Infrared Radiation Detector 42

The infrared radiation which has exited from a substrate-to-be-treated 12 is guided to the infrared radiation detector 42 via the infrared radiation condensing means 40. The infrared radiation detector 42 can be provided by a nitrogen-cooling infrared radiation detector of, e.g., InSb.

(h) Infrared Radiation Analyzing Means 60

The above-described infrared radiation detector 42 is a detector of, e.g., FT-IR apparatus. An output of the infrared radiation detector 42 can be indicated by absorption spectra corresponding to respective frequencies by the mechanism of Fourier Spectroscope using a double beam interferometer. As described in the basic principle that infrared radiation is incident on a substrate-to-be-treated 12 and undergoes multiple reflection inside the substrate to thereby monitor the substrate surfaces, frequency components of evanescent waves oozing when light reflects on the substrate surfaces are resonance-absorbed when they agree with molecular vibrational frequencies of organic contaminants on the substrate surfaces, and their absorption spectra are measured, whereby kinds and amounts of the organic contaminants can be determined. Kinds of organic contaminants and calibration curves are saved as separate data bases in the computing means 64 of the infrared radiation analyzing means 60. Monitored data are quantitized with reference to the data.

Information supplied by the infrared radiation analyzing means 60 is supplied to the controller 70 so that the radiation source 50 and the active species generator 54 are controlled via the radiation source control means 52 and the active species generator control means 56 to optimize cleaning conditions.

The computing means 64 stores information (reference data) for judging at what level of resonance absorption intensity of organic contaminants to be cleaned off the cleaning is stopped.

The computing means 64 compares measured data with the reference data to judge whether or not a level of measured data is lower than that of the reference data. When the level of the measured data is higher than that of the reference data, it is judged that an end point has not been reached, and the cleaning is continued. The cleaning is finished when the level of the measured data is lower than that of the reference data.

As the infrared radiation detector 42, an infrared radiation spectroscope using a diffraction grating may be used in place of the FT-IR apparatus.

[2] Dry Cleaning Method

The substrate treating method according to the present embodiment will be explained with reference to FIGS. 1, 8 and 9.

First, a substrate-to-be-treated 12 held in the substrate storage box 80 is placed on the substrate mount 10 via the substrata carrier system 84.

Then, the infrared radiation optical system and the substrate-to-be-treated 12 are aligned with each other by position control means (not shown) of the infrared radiation optical system and the substrate mount control means 16 so that infrared radiation emitted by the infrared radiation source 20 is incident on the declined part 14 of the substrate-to-be-treated 12, undergoes multiple reflection and exits and is guided to the infrared radiation detector 42. In this step, it is preferable that a position of the substrate-to-be-treated 12 is adjusted so that a maximum light amount of the infrared radiation can be detected by the infrared radiation detector 42.

Then, infrared radiation emitted by the infrared radiation source 20 is incident on the declined part 14 of the substrate-to-be-treated 12. Infrared radiation introduced into the substrate-to-be-treated 12 through the declined part 14 of the substrate-to-be-treated 12 repeats the internal multiple reflection while probing the surfaces of the substrate-to-be-treated, accumulating contamination information thereon, and exits from a position symmetric to the incident position of the infrared radiation.

Figure 11A:
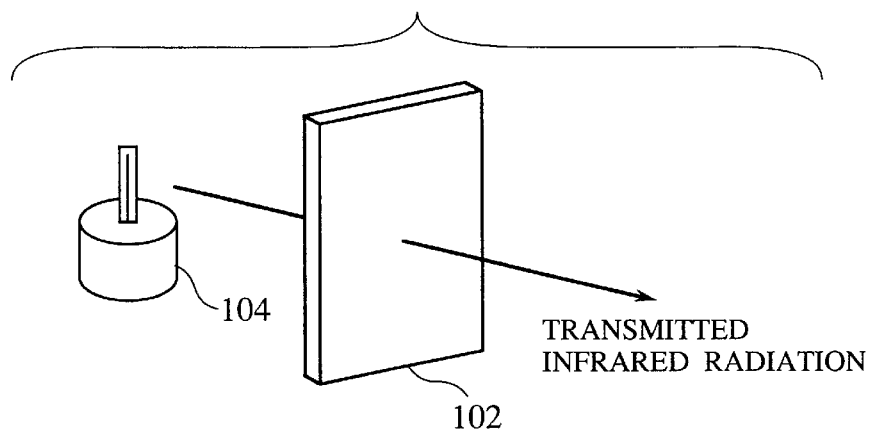
FIGS. 11A–11C are views explaining conventional surface state monitoring methods and apparatuses.
Figure 11B:
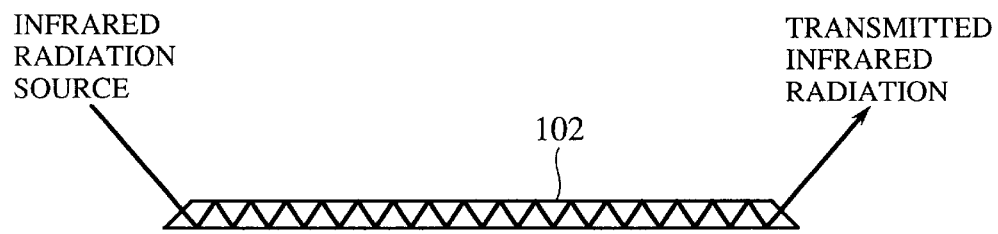
Figure 11C:
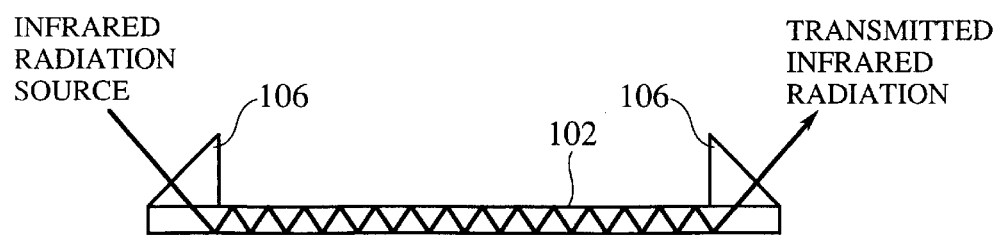

Then, the infrared radiation which has exited from the substrate-to-be-treated 12 is condensed by the infrared radiation condensing means 40 and is led to the spectroscope 62 through the infrared radiation detector 42. FIG. 11 show one example of spectra of the internal multiple reflection measured by the infrared radiation detector 42.

The above-described infrared radiation detector 42 is a detector of, e.g., FT-IR apparatus. An output of the infrared radiation detector 42 can be given by absorption spectra corresponding to respective frequencies by the mechanism of Fourier Spectroscope using a double beam interferometer. Frequency components of evanescent waves oozing when light reflects on the substrate surfaces are resonance-absorbed when they agree with molecular vibrational frequencies of organic contaminants on the substrate surfaces, and their absorption spectra are measured, whereby kinds and amounts of the organic contaminants can be determined. Kinds of organic contaminants and calibration curves are saved as separate data bases in the computing means 64 of the infrared radiation analyzing means 60. Monitored data are quantitized with reference to the data.

FIG. 9 shows absorbance spectra measured on a 200 mm silicon wafer with ethanol dropped on the surfaces. The absorbance spectra represent differences of the internal multiple reflection between spectra for the case that the surfaces of the substrate is free from contaminants and spectra for the case that the surfaces of the substrate has contaminants. As shown, peaks are detected at certain frequency bands. Based on the positions of the peaks, the peaks can be identified to correspond to O—H stretching and C—H stretching. Calibration curves indicating absorbances and contaminant amounts are measured in advance, so that amounts of organic contaminants can be identified based on peak intensities of the absorbances.

When required, the same measurement as described above is repeated after the substrate-to-be-treated 12 is rotated by the substrate mount 10 so as to monitor surface states substantially all over the surfaces.

This monitoring of surface states of a substrate-to-be-treated 12 is performed before the dry cleaning of the substrate-to-be-treated 12 or in the dry cleaning.

This in-situ monitoring permits surface states of a substrate-to-be-treated 12 to be correctly known, and the surface states can be fed back to treating conditions of the following dry cleaning. That is, based on a result of the analysis by the infrared radiation analyzing means 60, the controller 70 controls the radiation source 50, the active species generator 54 to adjust operation parameters, such as irradiation intensity, irradiation period of time, concentrations of active species, etc., whereby a substrate-to-be-treated can be dry-cleaned always under optimum cleaning conditions. The control of the cleaning conditions can be made by controlling the radiation source control means 52 and/or the active species generator control means 56 by the controller 70, based on output signals of the infrared radiation analyzing means 60.

An end point of the dry cleaning is judged by measuring a level of a resonance absorption intensity of contaminants, based on infrared radiation absorption spectra in the dry cleaning, and the level of the measured data is compared with a level of reference data stored in advance by the computing means 64. When the level of the measured data is higher than that of the level of the reference data, the dry cleaning is continued, and the dry cleaning is finished when the level of the measured data is lower than that of the level of the reference data. It is preferable that the reference data is suitably set in accordance with conditions (e.g., amounts of contaminants on a substrate-to-be-treated after the cleaning) required for the cleaning.

An end point of the cleaning is thus detected based on infrared radiation absorption spectra, whereby the end point of the cleaning can be accurately known based on decrease of a peak intensity corresponding to contaminants. Accordingly, a device formed on a substrate-to-be-treated 12 is protected from excessive damage. Furthermore, the dry cleaning on one substrate cannot be excessive, and can be continued on a next substrate. Accordingly high throughput can be obtained, and the cleaning can have uniform quality.

Then, the substrate-to-be-treated 12 which has been cleaned is carried to the substrate storage box 82 through the substrate carrier system 84. When required, one of the substrates stored in the substrate storage box 80 is carried through the substrate carrier system 84 onto the substrate mount 10, and the cleaning is continued on the substrate.

The use of FT-IR technique as the means for the in-situ monitoring of a substrate-to-be-treated 12 provides the following various merits.
1) The FT-IR technique is uncontiguous, and back-contamination by the monitoring system is absent.
2) The FT-IR technique is non-destructive monitoring means. That is, the FT-IR technique does not apply accelerated ions or accelerated electrons of high energy to a substrate but applies infrared radiation of low energy with a result that the substrate is not damaged. In addition, it is not necessary that a substrate is cut; for example, a 300 mm-silicon wafer of SEMI standards can be monitored as it is.
3) The monitoring is real time and has high monitoring speed. That is, probing light is passed through the inside of a substrate at light velocity. The monitoring is real time.
4) Signals of high signal/noise ratio (S/N ratio) can be detected. That is, infrared radiation repeatedly undergoes multiple reflection inside a substrate, whereby higher S/N ratios can be obtained, and higher detection sensitivity can be obtained.

Accordingly, the substrate treating apparatus includes such surface state monitoring means thus arranged, whereby surface states of a substrate-to-be-treated can be in-situ monitored uncontiguously and non-destructively at site of fabrication of a semiconductor device, and, based on results of the monitoring, treating conditions can be controlled, and end points can be detected.

As described above, according to the present embodiment, before a dry-cleaning treatment or in a dry-cleaning treatment surface states of a substrate-to-be-treated 12 are monitored by multiple reflection of infrared radiation incident on the declined part 14, and results of the monitoring are fed back to treating condition for the dry-cleaning. Thus, optimum treating conditions for the dry-cleaning can be always set.

Furthermore, an intensity of transmitted infrared radiation is compared with a prescribed value, whereby to accurately know an end point of a dry-cleaning treatment. Accordingly, a device fabricated on a substrate-to-be-treated 12 is protected from excessive damage.

In addition, the declined part 14 of a substrate-to-be-treated 12 on which infrared radiation is incident utilizes the end surface configuration of the substrate as it is. Accordingly it is not necessary to subject the substrate-to-be-treated 12 additionally to chemical etching or additional processing, or to introduce infrared radiation into the substrate-to-be-treated through prisms or others arranged above the substrate-to-be-treated 12. Thus, the apparatus and method according to the present embodiment are applicable to the in-situ monitoring at site of fabrication semiconductor devices.

[Second Embodiment]

The substrate treating method and apparatus according to a second embodiment of the present invention will be explained with reference to FIGS. 1 to 10. The same members of the present embodiment as those of the substrate treating method and apparatus according to the first embodiment are represented by the same reference numbers explanation of which is not repeated here to simplify the description.

Figure 10:
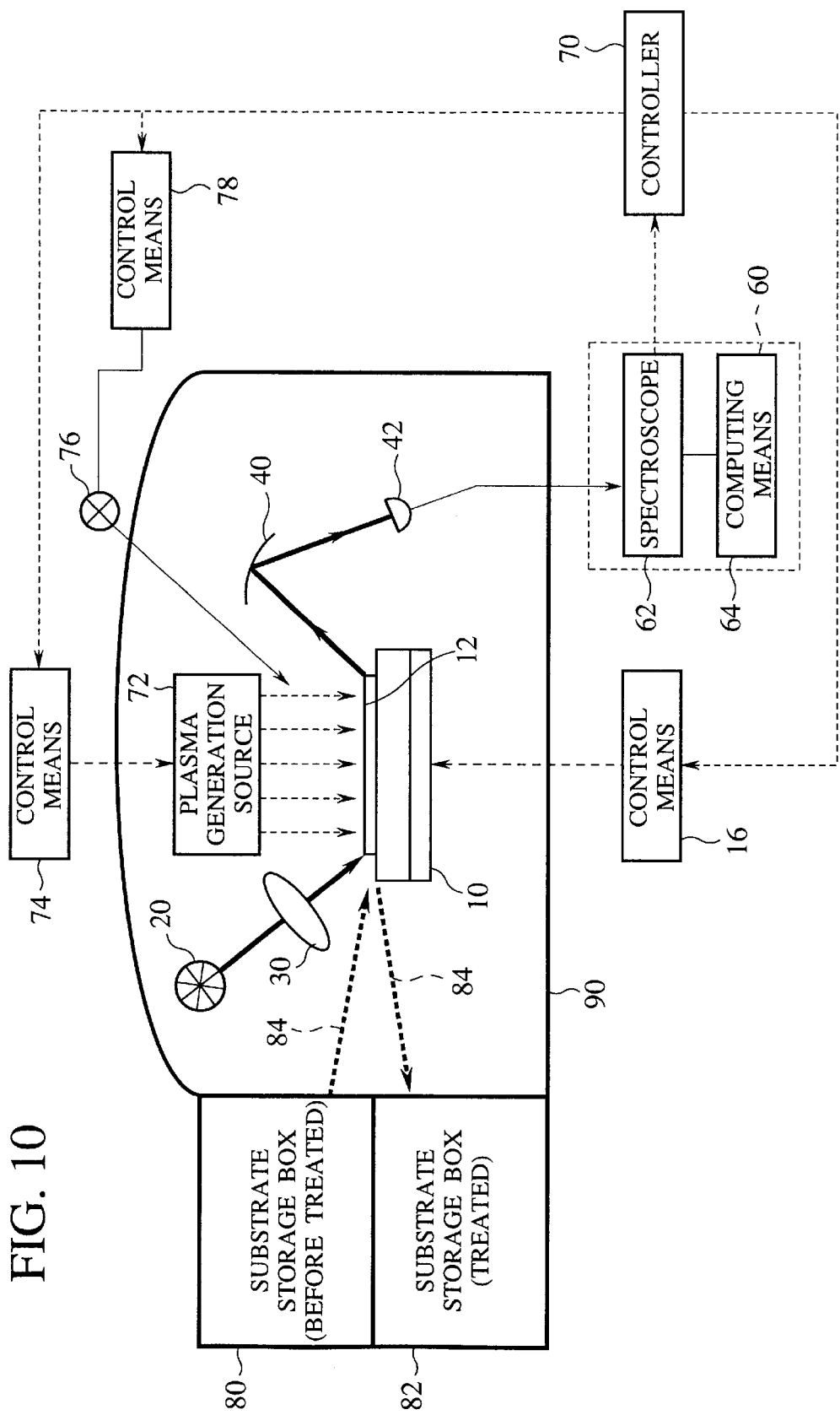
FIG. 10 is a diagrammatic view of the substrate treating apparatus according to a second embodiment of the present invention.

FIG. 10 is a diagrammatic view of the substrate treating apparatus according to the present embodiment.

[1] General Structure of the Apparatus

The substrate treating apparatus according to the present embodiment will be diagrammatically explained with reference to FIG. 10. In the present embodiment the present invention is applied to a plasma etching apparatus.

A substrate mount 10 for mounting a substrate-to-be-treated 12 for plasma etching is disposed in a vacuum vessel 90. A plasma generation source 72 which generates plasmas and applies the plasmas to the substrate-to-be-treated 12 is disposed above the substrate mount 10. Near the substrate-to-be-treated 12 there is disposed active species gas supply means 76 which generates active species (e.g., ozone, oxygen in the atomic state) which react with organic contaminants on the substrate-to-be-treated 12 to decompose them.

Near the substrate-to-be-treated 12 there is disposed an infrared radiation optical system including an infrared radiation source 20 which emits infrared radiation, infrared radiation condensing means 30 which condenses (converges or focuses) infrared radiation emitted by the infrared radiation source 20 into a prescribed shape and applies the condensed infrared radiation to the substrate-to-be-treated 12, infrared radiation condensing means 40 which condenses infrared radiation which has undergone multiple reflection inside the substrate-to-be-treated 12 and exited from the substrate-to-be-treated 12, and an infrared radiation detector 42 which detects the infrared radiation condensed by the infrared radiation condensing means 40.

The infrared radiation detector 42 is connected to an infrared radiation analyzing means 60 which analyzes a surface state of the substrate-to-be-treated 12 based on detected signals produced by the infrared radiation detector 42. The infrared radiation analyzing means 60 includes a spectroscope 62 which spectroscopes the infrared radiation detected by the infrared radiation detector 42, and computing means 64 in which data to be used in analyzing a surface state based on a spectroscopic result and judging an end point are accumulated and which performs required computations, based on the data and the result of the spectroscope 62.

The infrared radiation analyzing means 60 is connected to the plasma generation source 72 through a controller 70 and a plasma generation source control means 74, connected to the active species gas supply means 76 through the controller 70 and the active species gas control means 78, and connected to the substrate mount 10 through the controller 70 and a substrate mount control means 16. Based on results given by analysis of the infrared radiation analyzing means 60, the plasma generation source 72, the active species gas supply means 76 and the substrate mount 10 can be controlled.

In the optical path of the infrared radiation detector 42 and the optical path of infrared radiation to be detected there are provided means (not shown) for removing carbon dioxide ($CO_2$) in air, whose spectra overlap those of organic molecules. In the vacuum vessel 90 there are provided substrate storage boxes 80, 82 which store substrates-to-be-treated 12 after and before the treatment, and a substrate convey system 84 which conveys substrates-to-be-treated stored in the substrate storage box 80 to mount the same on the substrate mount 10, or conveys the dry-cleaned substrates-to-be-treated from the substrate mount 10 to the substrate storage box 82.

As described above, the substrate treating apparatus according to the present embodiment is characterized by the infrared radiation optical system for causing infrared radiation to undergo multiple scattering in a substrate-to-be-treated 12, whereby surface states of the substrate-to-be-treated are monitored. Specifically, by applying the infrared radiation optical system of the present embodiment, the surface of a substrate-to-be-treated 12 can be monitored in absorption states, chemical bonding states, and structures and thicknesses of the reactive layers can be in-situ monitored without additionally subjecting the substrate-to-be-treated 12 to chemical etching, end face processing or others or introducing infrared radiation into the substrate-to-be-treated through the prisms disposed above the substrate-to-be-treated 12.

Accordingly, the plasma etching apparatus including such infrared radiation optical system is thus arranged, whereby surfaces states of a substrate-to-be-treated 12 can be in-situ monitored in the step of the plasma etching. Based on results of the monitoring operation parameters can be suitably controlled to perform the plasma etching always in an optimum state. Furthermore, based on the results of the monitoring, an end point of the etching can be detected.

Then, the respective members of the substrate treating apparatus according to the present embodiment will be detailed. The members of the present embodiment which will not be described below may have the same constitutions as those of the substrate treating apparatus according to the first embodiment. About the details of the system of monitoring surface states it is recommended to see the specification of Japanese Patent Application No. 95853/1999 owned by the same assignee of the present application. The various monitoring systems described in the specification are applicable to the substrate treating method and apparatus according to the present embodiment.

(a) Plasma Generating Source 72

The plasma generating source 72 excites a gas introduced into the vacuum vessel 90 to generate plasmas.

Plasma contains positive and negative charged particles and is a group of particles which are neutral as a whole. Gas molecules, ions, electrons, and, in addition thereto, atoms which are metastable and energetically excited or polyatomic radicals (electrically neutral particles), light emitted from the plasma (vacuum ultraviolet) are present in a plasma.

On a semiconductor surface exposed to plasma physical and chemical reactions go on with radicals, ions, electrons, ultraviolet. For example, organic substances (hydrocarbon compounds) on a semiconductor substrate can be removed by the use of Oxygen plasma. Oxygen plasma can be generated by introducing into the vacuum vessel 90 oxygen gas by the active species gas supply means 76 and supplying sufficient energy (e.g., 13.56 high frequency power) to cause the reaction

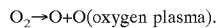
$O_2 \rightarrow O+O$(oxygen plasma).

When a hydrocarbon compound and an oxygen plasma react with each other on a substrate-to-be-treated 12, the reaction

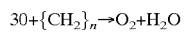
$3O+\{CH_2\}_n \rightarrow O_2+H_2O$ takes place, and the hydrocarbon compound $\{CH_2\}_n$ is transformed to gaseous low-molecular weight compound $CO_2$, and $H_2O$ (the same process as combustion) and exhausted to be completely removed.

The plasma generating source 72 is provided optimumly for such plasma reaction by, e.g., a parallel plate-type plasma generating source which comprises a plate electrode disposed parallel with the substrate mount 10 for generating plasmas between the substrate mount 10 and the electrode by high-frequency excitation, or by a down flowtype plasma generating source which comprises a plasma generating chamber and a reaction chamber separated from each other for feeding only active species onto a substrate-to-betreated. The plasma generating source 72 may be selected out of TCP (Transformer Coupled Plasma) type, IPC (Inductively Coupled Plasma) type, helicon wave-type, micro wave excitation type, etc. The plasma generating source 72 may be provided by the same one as used in the usual plasma etching apparatuses.

In the substrate treating apparatus according to the present embodiment, a state of the plasma generated by the plasma generating source 72 can be suitably adjusted in accordance with results of the in-situ monitoring of surface states of a substrate-to-be-treated 12 by the infrared radiation analyzing means 60.

The plasma etching process is determined by a dynamic balance between an influx of radical ions transferred from gaseous phase, and adsorption, reaction and elimination processes of an outflux from the surface of a substrate-to-be-treated 12. Accordingly, adsorption states, chemical bonding states, structures and thicknesses of the reactive layers are monitored in-situ by the infrared radiation optical system, whereby results of the in-situ monitoring can be fed back for setting optimum plasma etching conditions and detection of end points of the plasma etching.

Such feed-back control can be performed by controlling the plasma generation source control means 74 by the controller 70, based on output signals of the infrared radiation analyzing means 60.

The plasma etching according to the present embodiment is also applicable to removal of organic contaminants and chemical contaminants adhered to the surface of a substrate-to-be-treated 12, i.e., the dry cleaning.

(b) Active Gas Supply Means 76

The active species gas supply means 76 supplies an etching gas for the plasma etching of a substrate-to-be-treated 12.

An etching gas to be introduced into the vacuum vessel 90 by the active species supply means 76 is selected suitably to generate a required plasma, whereby the plasma etching can be performed on various substrates-to-be-treated 12. An etching gas to be introduced into the active species gas supply means 76 can, e.g., ozone, oxygen in the atomic state or others when an object to be etched is an organic substance.

The active species gas supply means 76 is connected to the controller 70 through the active species gas control means 78. Accordingly, adsorption states, chemical bonding states, structures and thicknesses of the reactive layers are monitored in-situ by the infrared radiation optical system, whereby results of the in-situ monitoring can be fed back for setting optimum plasma etching conditions and detection of end points of the plasma etching.

Such feed-back control can be performed by controlling the active species gas control means 78 or the above-described plasma generation source 72 by the controller 70, based on output signals of the infrared radiation analyzing means 60.

(c) Infrared Radiation Analyzing Means 60

The above-described infrared radiation detector 42 is a detector of, e.g., FT-IR apparatus. An output of the infrared radiation detector 42 can be indicated by absorption spectra corresponding to respective frequencies by the mechanism of Fourier Spectroscope using a double beam interferometer. As described in the basic principle that infrared radiation is incident on a substrate-to-be-treated 12 and undergoes multiple reflection inside the substrate to thereby monitor the substrate surfaces, frequency components of evanescent waves are resonance-absorbed when they agree with molecular vibrational frequencies of organic contaminants on the substrate surfaces, and their absorption spectra are analyzed, whereby adsorption states, chemical bonding states and structures and thicknesses of the reactive layers can be determined. Calibration curves, etc. for determining them are saved as separate data bases in the computing means 64 of the infrared radiation analyzing means 60. Monitored data are quantitized with reference to the data.

Information given by the infrared radiation analyzing means 60 is supplied to the controller 70 so that the plasma generation source 72 and the active species gas supply means 76 are controlled through the plasma generation source control means 74 and the active species gas control means 78 so as to optimize etching conditions.

The computing means 64 compares measured data with the reference data to judge whether or not a level of measured data is lower than that of the reference data. When the level of the measured data is higher than that of the reference data, it is judged that an end point has not been reached, and the etching is continued. The etching is finished when the level of the measured data is lower than that of the reference data.

As the infrared radiation detector 42, an infrared radiation spectroscope using a diffraction grating may be used in place of the FT-IR apparatus.

[2] Plasma Etching Method

The substrate treating method according to the present embodiment will be explained with reference to FIG. 10.

A substrate-to-be-treated 12 held in the substrate storage box 80 is mounted onto the substrate mount 10 via the substrate carrier system 84.

Then, as described in the first embodiment, the infrared radiation optical system and the substrate-to-be-treated 12 are aligned with each other by position control means (not shown) of the infrared radiation optical system and the substrate mount control means 16 so that infrared radiation emitted by the infrared radiation source 20 is incident on the declined part 14 of the substrate-to-be-treated 12, undergoes multiple reflection and exits and is guided to the infrared radiation detector 42.

Then, infrared radiation emitted by the infrared radiation source 20 is incident on the declined part 14 of the substrate-to-be-treated 12. Infrared radiation introduced into the substrate-to-be-treated 12 through the declined part 14 of the substrate-to-be-treated 12 repeats the internal multiple reflection while probing the surfaces of the substrate-to-be-treated, accumulating information of the substrate surface and is exited from a position symmetrical to the incident point of the infrared radiation.

Then, the infrared radiation which has exited from the substrate-to-be-treated 12 is condensed by the infrared radiation condensing means 40 and is detected by the infrared radiation detector 42.

The infrared radiation detector 42 is a detector of, e.g., FT-IR apparatus. An output of the infrared radiation detector 42 can be given by absorption spectra corresponding to respective frequencies by the mechanism of Fourier Spectroscope using a double beam interferometer. Frequency components of evanescent waves oozing when light reflects on the substrate surfaces are resonance-absorbed when they agree with molecular vibrational frequencies of substances on the substrate surfaces, and their absorption spectra are analyzed, whereby adsorption states, chemical bonding states, structures and thicknesses of the reactive layers, etc on the surface of the substrate-to-be-treated 12 can be determined. Calibration curves are saved as separate data bases in the computing means 64 of the infrared radiation analyzing means 60. Monitored data are quantitized with reference to the data.

When required, the same measurement as described above is repeated after the substrate-to-be-treated 12 is rotated by the substrate mount 10 so as to monitor surface states substantially all over the surfaces.

Such monitoring of surface states of a substrate-to-be-treated 12 is performed before the plasma etching of the substrate-to-be-treated 12 or in the plasma etching. Thus, surface states of a substrate-to-be-treated 12 can be accurately monitored in-situ, and the surface states can be fed back to treating conditions for further continuing the plasma etching. That is, operation control for the plasma generation, improving spacial homogeneity and retaining a plasma intensity corresponding to information, such as adsorption states, chemical bonding states, structures and thicknesses of the reaction layers, etc., whereby the substrate-to-be-treated 12 can be plasma-etched always under optimum conditions. The control of conditions of the plasma etching can be controlled by controlling the plasma generation source control means 74 and/or the active species gas control means 78 by the controller 70, based on output signals of the infrared radiation analyzing means 60.

The analysis of surface states by the infrared radiation optical system can quantitize and identify organic contaminants and chemical contaminants adhered on a substrate-to-be-treated 12. Accordingly, the feedback is applicable to the plasma etching for the dry cleaning for removing such contaminants.

An end point of the etching is judged by measuring a level of a resonance absorption intensity of contaminants, based on infrared radiation absorption spectra in the etching, and the level of the measured data is compared with a level of reference data stored in advance by the computing means 64. When the level of the measured data is higher than that of the level of the reference data, the etching is continued, and the etching is finished when the level of the measured data is lower than that of the level of the reference data. It is preferable that the reference data is suitably set in accordance with characteristics (e.g., an amount of a substance-to-be-etched on a substrate-to-be-treated after the etching) required for the etching.

As described above, according to the present embodiment, before the plasma etching or in the plasma etching surface states of a substrate-to-be-treated 12 are monitored by multiple reflection of infrared radiation incident on the declined part 14 of the substrate-to-be-treated 12, and results of the monitoring are fed back to treating conditions of the plasma etching, whereby optimum treating conditions of the plasma etching can be always set.

An end point of the etching can be accurately known by comparing an intensity of transmitted infrared radiation to a reference value. Thus, a device fabricated on a substrate-to-be-treated 12 is protected from being damaged.

In addition, the declined part 14 of a substrate-to-be-treated 12 on which infrared radiation is incident utilizes the end surface configuration of the substrate as it is. Accordingly it is not necessary to subject the substrate-to-be-treated 12 additionally to chemical etching or processing, or to introduce infrared radiation into the substrate-to-be-treated through prisms or others arranged above the substrate-to-be-treated 12. Thus, the apparatus and method according to the present embodiment are applicable to the in-situ monitoring at site of fabrication semiconductor devices.

In the first and the second embodiment the substrate-to-be-treated 12 is a silicon substrate, but is not limited to a silicon substrate. Germanium substrate and compound semiconductor substrates, as of GaAs, etc., may be similarly used as the substrate-to-be-treated 12. The monitoring is not limited to semiconductor substrates and may be used on the same principle to glass substrate of liquid crystal displays.

In the above-described embodiments the function of monitoring surface states of a substrate-to-be-treated by the infrared radiation optical system is applied to the dry cleaning apparatus and the plasma etching apparatus but may be applied to other semiconductor device fabrication apparatus.

For example, the surface state monitoring means of the present invention is provided in a film forming apparatus for forming required films on a semiconductor substrate, whereby states of the substrate surface can be monitored in-situ in pre-processing for forming a film, e.g., a thermal cleaning step or a reverse sputtering step. The thus-arranged film forming apparatus can optimize conditions of pre-processing before forming a film.

What is claimed is:

1. A substrate treating apparatus for monitoring and treating a substrate-to-be-treated, comprising:

a substrate treating means for subjecting the substrate-to-be-treated to a required treatment;

a surface state monitoring means including;

an infrared radiation condensing means for condensing infrared radiation emitted by an infrared radiation source onto an outer peripheral part of the substrate-to-be-treated, an infrared radiation detecting means for detecting the infrared radiation which has undergone multiple reflection inside the substrate-to-be-treated where frequency components of the infrared radiation are resonance-absorbed when they agree with molecular vibrational frequencies of contaminants on the surface of the substrate-to-be-treated and exited from the substrate-to-be-treated, and an infrared radiation analyzing means for analyzing absorption spectra of the infrared radiation detected by the infrared radiation detecting means, wherein the surface state monitoring means monitoring in-situ a surface state of the substrate-to-be-monitored when the substrate-to-be-treated is treated by the substrate treating means; and a control means for controlling the substrate treating means, based on the surface state of the substrate-to-be-treated, which was monitored by the surface state monitoring means.

2. A substrate treating apparatus according to claim 1, wherein, the infrared radiation analyzing means monitors the surface state of the substrate-to-be-treated, based on a spectroscopic results of the absorption spectra given by Fourier transform spectroscopy.

3. A substrate treating apparatus according to claim 1, wherein, the infrared radiation analyzing means monitors the surface state of the substrate-to-be-treated, based on a spectroscopic result of the absorption spectra given by infrared spectroscopy using a diffraction lattice.

4. A substrate treating apparatus according to claim 1, wherein, the substrate treating means is a cleaning means for decomposing and removing a contaminant adhered to the substrate-to-be-treated by light irradiation, the surface state monitoring means monitors and determines a kind and/or an amount of the contaminant adhered to the substrate-to-be-treated, and the control means controls treating conditions for treating the substrate-to-be-treated by the cleaning means, based on the kind and/or the amount of the contaminant given by the surface state monitoring means.

5. A substrate treating apparatus according to claim 4, wherein, the control means controls an irradiation intensity or an irradiation period of time of the light to be irradiated to the substrate-to-be-treated based on the kind and/or the amount of the contaminant given by the surface state monitoring means.

6. A substrate treating apparatus according to claim 4, wherein, the cleaning means includes an active species supply means for supplying an active species which reacts with the contaminant to the substrate-to-be-treated.

7. A substrate treating apparatus according to claim 6, wherein, the control means controls a supply amount of the active species to be supplied by the active species supply means, based on the kind and/or the amount of the contaminant given by the surface state monitoring means.

8. A substrate treating apparatus according to claim 1, further comprising:

an end point detecting means for detecting an end point of the substrate treatment based on the kind and/or the amount of the contaminant given by the surface state monitoring means.

9. A substrate treating apparatus according to claim 8, wherein, the end point detecting means judges whether or not the substrate-to-be-treated has arrived at the end point of the treatment by comparing a monitored level of resonance absorption intensity of the infrared radiation of the contaminant with a prescribed reference level.

10. A substrate treating apparatus according to claim 8, wherein, the control means stops the treatment of the substrate-to-be-treated based on end point information given by the end point detecting means.

11. A substrate treating apparatus according to claim 1, wherein, the substrate treating means is an etching means for etching the substrate-to-be-treated by applying a plasma to the substrate-to-be-treated, and the control means controls etching conditions for etching the substrate-to-be-treated by the etching means based on the surface state of the substrate-to-be-treated monitored by the surface state monitoring means.

12. A substrate treating apparatus according to claim 11, wherein, the control means controls a state of the plasma based on the surface state of the substrate-to-be-treated monitored by the surface state monitoring means.

13. A substrate treating apparatus according to claim 11, wherein, the surface state monitoring means monitors an adsorption state of an influx or an outflux, a chemical bonding state or a structure of a reactive layer on the surface of the substrate-to-be-treated.

14. A substrate treating apparatus according to claim 11, wherein, the surface state monitoring means monitors and determines a kind and/or an amount of a contaminant adhered to the surface of the substrate-to-be-treated.

15. A substrate treating apparatus according to claim 11, further comprising:

an end point detecting means for detecting an end point of the etching of the substrate-to-be-treated based on the surface state of the substrate-to-be-treated monitored by the surface state monitoring means.

16. A substrate treating apparatus according to claim 15, wherein, the control means stops the treatment of the substrate-to-be-treated based on end point information given by the end point detecting means.

17. A substrate treating apparatus according to claim 1, wherein, the substrate-to-be-treated has a declined part on an outer peripheral part thereof, which is formed by chamfering a corner defined by the surface of the substrate-to-be-treated and an outer peripheral surface thereof, and the infrared radiation condensing means condenses the infrared radiation onto the declined part of the substrate-to-be-treated.

18. A substrate treating apparatus according to claim 1, wherein, the infrared radiation condensing means condenses the infrared radiation into a circular or an empirical focus.

19. A substrate treating apparatus according to claim 1, wherein, the infrared radiation source has a light source for emitting the infrared radiation, the light source is covered by a vessel to be sealed from active species thereby preventing explosion associated with the active species.

* * * * *